(12) United States Patent
Bell et al.

(10) Patent No.: US 6,774,102 B1
(45) Date of Patent: Aug. 10, 2004

(54) EXTRACORPOREAL ENDOTOXIN REMOVAL METHOD

(75) Inventors: Carl-Martin Bell, Hechingen (DE); Markus Storr, Leinfelden-Echterdingen (DE); Werner Beck, Rottenburg (DE)

(73) Assignee: Gambro Dialysatoren GmbH & Co. KG, Hechingen (DE)

(*) Notice: Subject to any disclaimer, the term of this patent is extended or adjusted under 35 U.S.C. 154(b) by 242 days.

(21) Appl. No.: 09/677,375

(22) Filed: Sep. 15, 2000

Related U.S. Application Data

(60) Provisional application No. 60/156,649, filed on Sep. 29, 1999.

(51) Int. Cl.[7] .............................................. A61K 38/02
(52) U.S. Cl. ...................... 514/2; 530/334; 604/5.01; 604/5.02; 604/5.03; 604/5.04
(58) Field of Search ................... 514/2; 530/334; 604/5.01, 5.02, 5.03, 5.04

(56) References Cited

U.S. PATENT DOCUMENTS

| | | | |
|---|---|---|---|
| 5,061,626 A | * 10/1991 | Baldo et al. ................ | 435/174 |
| 5,186,826 A | 2/1993 | Otto et al. ................. | 210/198.2 |
| 5,599,901 A | * 2/1997 | Kauvar ...................... | 530/328 |
| 5,780,594 A | * 7/1998 | Carter ....................... | 530/363 |
| 6,194,543 B1 | * 2/2001 | Florence et al. ............ | 530/300 |
| 6,344,360 B1 | * 2/2002 | Colvin et al. ............... | 436/94 |

FOREIGN PATENT DOCUMENTS

| | | |
|---|---|---|
| EP | 0 028 937 | 5/1981 |
| EP | 0 107 119 | 4/1983 |
| EP | 0 129 786 | 2/1985 |
| EP | 0 494 848 | 7/1992 |
| EP | 0 787 500 | 6/1997 |
| EP | 0 800 862 | 10/1997 |
| WO | WO 92/11847 | 7/1992 |
| WO | 94/02506 | * 2/1994 |
| WO | 95/00540 | * 1/1995 |
| WO | WO 95/05393 | 2/1995 |
| WO | WO 96/38410 | 12/1996 |
| WO | WO 96/41185 | 12/1996 |

OTHER PUBLICATIONS

Mitzner et al. (1993) "Extracorporeal Endotoxin Removal by Immobilized Polyethylenimine" *Artificial Organs* 17(9):775–781.

Staubach, K. H. et al. (1997) "Extracorporeal Adsorption of Endotoxin" *Therapeutic Apheresis* 1(1):67–74.

von Appen, K. et al. (1996) "Microspheres Based Detoxification System: A New Method in Convective Blood Purification" *Artificial Organs* 20(5):420–425.

* cited by examiner

*Primary Examiner*—Christopher S. F. Low
*Assistant Examiner*—David Lukton
(74) *Attorney, Agent, or Firm*—Greenlee Winner and Sullivan, P.C.

(57) ABSTRACT

This invention describes blood treating material having the capacity to selectively remove endotoxin and cytokine inducing substances from blood or plasma by extracorporeal adsorption for therapeutic septic shock treatment. The endotoxin adsorption ligands of the invention are oligopeptides synthesized from amino acids having a pk>7.2 such as arginine, lysine or histidine, using a polycondensation step such that the resultant oligopeptides exhibit a high degree of polydispersity. Also provided are methods and devices using an adsorbent having a polydisperse oligopeptide of the invention immobilized on a solid state support medium for removing endotoxin from the blood of human or animal subject.

18 Claims, 3 Drawing Sheets

EXTRACORPOREAL ENDOTOXIN REMOVAL METHOD

CROSS REFERENCE TO RELATED APPLICATIONS

This application claims priority from U.S. Provisional Patent Application No. 60/156,649 filed Sep. 29, 1999.

ACKNOWLEDGMENT OF FEDERAL RESEARCH SUPPORT

Not applicable.

BACKGROUND OF THE INVENTION

The invention relates to blood treating material having the capability of selectively removing endotoxin and cytokine inducing substances from blood or plasma by extracorporeal adsorption for therapeutic septic shock treatment.

Endotoxins are lipopolysaccharides from gram-negative bacteria and are the leading cause of sepsis and septic shock, having mortality rates of more than 50%. Endotoxins can persist in blood subsequent to infection even in the absence of live bacteria. Endotoxin molecules have a highly conserved region, which consists of Lipid-A moiety comprising several long fatty acid chains and sugar rings with at least two negatively charged phosphate groups. The Lipid-A moiety is connected to polysaccharide chains which vary greatly depending on bacteria type. The pathological effect is mainly derived from the Lipid-A moiety of the molecule. The accessibility of the Lipid-A moiety is largely modulated by the nature of the polysaccharide chains and the surrounding media, including such factors as salinity, water, sugar molecules, plasma, blood, pH, detergents, and the like. For example, high salt concentration leads to micellar and other supermolecular structures of endotoxins, resulting in different activities.

Endotoxin is assayed by measuring its cytokine-inducing effect on CD14-positive leucocytes, to produce, e.g. TNF-α, which can be analyzed by an ELISA technique using a commercially available kit, e.g. R&D Systems, Bad Homburg, Germany or by an LAL induced chromogenic substrate reaction (Chromogenics, Moeldwagen, Sweden). The molecular weight of endotoxin ranges from 5000 Da to some millions Da depending on the polysaccharide chain length and its supermolecular structure.

Most extracorporeal removal strategies have exploited the negatively charged phosphate groups of endotoxin using positively charged adsorbent materials immobilized on a variety of substrates. Kodama, et al. (EP 0107119, EP 0129786) disclosed polycationic Polymyxin B covalently immobilized on polystyrene fibers and described adsorbing endotoxins from blood in a device filled with woven fibers of such material. Otto, et al. (EP 424698) also disclosed immobilized polycationic Polymyxin B on poly (comethacrylate) beads for adsorbing endotoxin from blood. Falkenhagen, et al. [*Artificial Organs* (1996) 20:420] described adsorbing endotoxin from plasma on polycationic polyethyleneimine-coated cellulosic beads. Mitzner, et al. [*Artificial Organs* (1993) 17(9):775] described polyethyleneimine and Polymyxin B immobilized on macroporous cellulose beads for endotoxin removal from plasma. A product incorporating the Kodama technique has been marketed in Japan; however, the fact that Polymyxin B is strongly nephrotoxic has been a drawback preventing registration in other countries due to the risk of Polymyxin B leaching into blood. Polyethyleneimine as an endotoxin ligand has the twin disadvantages that it strongly adsorbs heparin and also interacts with platelets, leading to coagulation problems in an in vivo application. The potential for adsorbing plasma proteins poses a significant problem for developing an endotoxin adsorbent that is both specific and selective.

European applications (EP 0494848, EP 0129786, Pharmacia Upjohn) disclosed endotoxin removal using an arginine ligand on sepharose. Whereas in vitro trials appeared promising, no further development appears to have been made. Anspach (WO97/33683, DE 19609479) described the immobilization of cationic ligands such as polylysine, N,N-diethylaminoethane, lysine, arginine, histidine or histamine onto polyamide microfiltration membranes and disclosed data on removal of up to about 50% endotoxin from protein solutions. However, applicability was restricted to solutions having a lower protein content than blood or plasma. Hoess, et al. (WO 95/05393) described a peptide having endotoxin adsorbent property. The peptide was composed of hydrophilic, positively charged aminoacids alternated with hydrophobic aminoacids. No data was reported on endotoxin adsorption from blood or plasma. Evans, et al. (WO 96/41185) described immobilizing amidine groups on macroporous beads such that the groups had a specific spacing between the positively charged centers. The material was reportedly suitable for endotoxin removal from plasma and other fluids; however, the material does not appear to be commercially available. Otto, et al. (EP application 0858831) disclosed endotoxin removal from whole blood using albumin as a ligand covalently immobilized onto macroporous polymethyl methacrylate beads. Although in vitro data under static conditions in plasma showed excellent endotoxin adsorption capacity, when applied to whole blood under flowing conditions as in a therapeutic application, the endotoxin removal behavior was very restricted, perhaps due to the weak binding of endotoxin onto immobilized albumin.

Other workers have explored the use of non-selective surfaces for removing endotoxin removal from plasma. Ash, et al. (Biologic DTPF-system TM, ISFA-congress, Saarbrüken/Germany, Apr. 15–19, 1999) treated endotoxin containing plasma in vitro with fine powdered charcoal, having no ligand, with a surface area of approximately 1000 $m^2/g$ charcoal/10 ml plasma. Although high endotoxin removal was reported, the report did not give more details as to what other components had been removed, including beneficial substances. Tetta, et al. (EP 0787500) described the use of positively charged ion-exchange beads for endotoxin removal from plasmas and reported 90% removal in animal trials.

In summary one approach is to remove as much endotoxin as possible simply by using very large adsorbent areas. However, non-specific binding can result in collateral removal of normal blood components such as certain antibodies and coagulation factors. The collateral removal is undesirable. Also, the use of non-specific binding materials is restricted to treatment of plasma, in order to avoid cell activation. Non-specific binding materials are considered impractical for a whole-blood application due to the potential risk of unexpected side reactions.

A different approach is represented by the disclosures of Kodama et al. supra or Otto et al supra based on the use of specific-binding ligands such as polymyxin B or histidine. While such ligands demonstrate sufficient specificity to avoid collateral removal of blood components, the binding capacity is variable across the range of endotoxins likely to be encountered. In order to compensate for low binding capacity a large adsorption chamber might be required, necessitating an unacceptably large extracorporeal blood volume to achieve rapid endotoxin clearance. The lack of binding capacity for a polymyxin B ligand adsorbent was revealed in animal studies in which the adsorbent was only able to clear the endotoxin for a limited time [Otto et al (1997) *Therapeutic Apheresis* 1:67]. Although the animals lived somewhat longer than untreated controls, the survival rate was not affected.

The use of serum albumin as an adsorbent has been reported. Non-covalent attachment of albumin to bead-type support materials has been reported by Hirae et al. EP 800862, and Suzuki et al EP 028937. Covalently attached albumin has also been disclosed (Otto, EP 848831). The rationale for using albumin is that it already fictions as a binding and transport protein in the bloodstream. The practical use of immobilized albumin is limited by the fact that albumin does not bind endotoxin with sufficient avidity.

Hemodialysis membranes with higher protein adsorption as e.g. AN69 (Gambro-Hospal) are considered to be good surfaces for very low incidence of sepsis related reactions, due to their endotoxin and cytokine adsorption capability.

SUMMARY OF THE INVENTION

The problem solved by the present invention is to devise endotoxin adsorption ligands which, on the one hand, have sufficient heterogeneity to effectively adsorb a large variety of endotoxins, while at the same time having sufficient specificity for endotoxins generally to avoid adsorbing other physiologic components of blood, in order not to cause inappropriate side reactions. For this, polycationic species have been synthesized from amino acids which are positively charged at physiological pH of 7.2, e.g. arginine, lysine, or histidine using a polycondensation step in diluted solution in water, such that a very high degree of polydispersity (polycondensation degree, degree of branching, coiling state) results. The broadly distributed oligopeptides can be immobilized on a solid state medium, for example a porous, activated substrate including beads or membranes using conventional coupling reagents such as cyanuric chloride, carbonyldiimidazol, promcyan or water soluble carbodiimide, washed, filled in a housing and sterilized. Surprisingly, the high degree of oligopeptide heterogeneity corresponds to the high degree of heterogeneity of endotoxin resulting in a high capacity for removal of endotoxins from different sources.

Extracorporeal removal of endotoxin from blood of a human or animal subject is accomplished by contacting the blood with an adsorbent composed of a polydisperse oligopeptide of the invention immobilized on a solid state support medium. The support medium is preferably a porous material such as a membrane, particle bed or fiber mat having porosity sufficient to allow passage of blood cells therethrough. Particularly preferred support materials are in the form of beads, which can be filled into a container, the beads having a size sufficient to provide the requisite porosity when packed into a column or filter bed. Examples of suitable bead materials known in the art are provided below.

A device for extracorporeal removal of endotoxin from whole blood can be constructed according to general principles known in the art. The basic components of such a device are a container which is constructed to contain and retain the adsorbent having endotoxin ligand immobilized on a solid phase support medium as described, an inlet and an outlet. The inlet and outlet are positioned with respect to the adsorbent such that blood entering the inlet must contact the adsorbent before exiting through the outlet. Preferably, the geometry of the device is designed to maximize contact of blood with adsorbent during passage through the device. A variety of such designs are known in the art. For example, the device can be a hollow cylinder packed with adsorbent beads, having the inlet at one end and the outlet at the opposite end. Other devices, such as microtubule arrays, can be constructed. All such variations of container geometry and volume and of adsorbent contained therein can be designed according to known principles.

A process for removing endotoxin from the blood of a human or animal subject includes removing a portion of blood from the subject, contacting the blood with an adsorbent according to the invention, whereby the endotoxin binds to the adsorbent, then returning the blood to the subject. Preferably the process is carried out in a continuous flow. The location of the blood vessels of the subject at which blood is removed and returned can be different from one another or the same. In the latter case, single needle techniques are known in the art which reduce the invasiveness of the process.

The duration of treatment will depend upon the endotoxin concentration in the blood, the type of endotoxin present, the capacity of the adsorbent to clear the endotoxin, flow rate and the like, all of which can be monitored and adjusted as is known in the art.

The invention provides broadly distributed: and/or highly branched peptides with a molecular weight range of 500 to 50,000 Da, composed of one or more amino acids which are positively charged at physiological pH (isoelectric point>7.2).

DETAILED DESCRIPTION OF THE INVENTION

Figure 1:
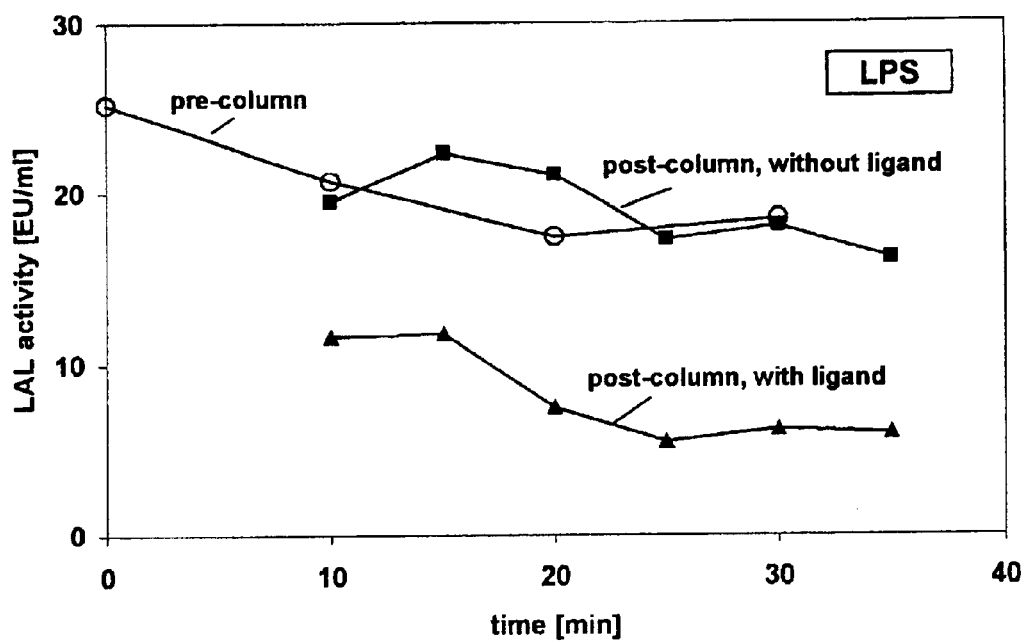
FIG. 1 shows the levels of lipopolysaccharide (LPS) in human blood at various time points before (0) and after (▼) passage through a column containing polydisperse arginine oligomers immobilized on beads (see Example 2 for details). The LPS contents were determined using chromogenic Limulus Amoebocyte Lysate (LAL) test. Also shown are the LPS contents in human blood (labeled as ■) after passage through a column which did not contain polydisperse arginine oligomers.

In general, the terms and phrases used herein have their art-recognized meaning, which can be found by reference to standard texts, journal references and contexts known to those skilled in the art. The following definitions are provided to clarify their specific use in the context of the present invention.

Polydispersity is herein defined to include not only the conventional definition, $M_w/M_n$ (ratio of weight average molecular weight $M_w$ to number average molecular weight, $M_n$) but also to include heterogeneity in degree of branching, as well. Polydispersity as herein defined can be assessed by thin layer chromatography, under conditions where chromatographic mobility ($R_f$) is increased as charge density is reduced due to branching, compared to a standard material of known polydispersity.

"Oligopeptide" as used herein refers to a polymer containing more than one amino acid, generally up to about twenty residues, linked together by peptide bonds. Linear oligopeptide refers to an oligopeptide formed by amide bonds between the alpha-carboxyl and alpha-amino groups of adjacent residues and branched oligopeptide refers to an oligopeptide formed by amide bonds involving one or more non-alpha-amino groups.

Preparation of Polydisperse Arginine-ligand 5.2 g L-arginine (Sigma, A-5006) were dissolved in 26 g Reverse Osmosis- (RO) treated water at 40° C. 4.16 g WSC.HCl (1-Ethyl-3-(3-dimethylaminopropyl)-carbodiimide, Novabiochem, 01-62-011) was dissolved at room temperature in 26 g RO-treated water. These two solutions were mixed and stirred over a reaction time of 18 hrs. at room temperature.

The polycondensation was carried out at pH 11.5. Given the approximate pK of 12.5 for the guanido group of arginine, approximately 10% of the guanido groups are unprotonated and therefore available to react in a chain-branching reaction. The degree of branching was regulated by adjusting the reaction pH. The use of the water-soluble carbodiimide beads leads to racemization such that both D- and L- amino acids were present in the resulting oligopeptides.

The degree of polydispersity was measured by thin layer chromatography on silica gel (Kieselgel 60F, Merck) using as mobile phase $CHCl_3:CH_3OH:NH_3/40:40:20$, (45% $NH_3$ solution). The results are shown in Table I.

TABLE I

| Ligand | $R_f$ (Kieselgel 60 F., Merck: stationary phase) $CHCl_3:CH_3OH:NH_3/40:40:20$ (45% $NH_3$ solution) |
|---|---|
| Polyarginine, Mw/Mn = 1.2 (Sigma) | <0.1 |
| L-arginine | 0.3 |
| Polydisperse arginine ligand | 0.6 |

The foregoing reactions can also be carried out using lysine or histidine or other amino acids having a net positive charge at pH>7.2, or by a polycondensation of mixtures of such amino acids. As with the exemplified polyarginine, the polydispersity can be controlled by selection of the reaction pH to control the proportion of unprotonated amino groups available to serve as branch points, as will be understood in the art.

The degree of polydispersity of the oligopeptides made according to the instant invention can be measured by any art-recognized method. Chromatographic methods known to measure the degree of polydispersity can be used to assess the oligopeptides of the invention together with a standard material of known polydispersity. Polydispersity can also be conveniently assessed by thin layer chromatography as shown in Table I, where the $R_f$ value of a composition made according to the invention was compared with the $R_f$ value of a standard material of known polydispersity. Oligopeptides suitable for the invention are sufficiently polydisperse if they have an RF value of 0.4 or greater, preferably 0.6 or greater as measured by thin layer chromatography on silica gel (e.g. Kieselgel 60F) using a solvent phase $CH_3Cl_3:CH_3OH:NH_3/40:40:20$ in 45% $NH_3$ solution.

Conditioning of Substrate

1. Activated Beads:

The following commercially available activated beads can be conditioned for immobilization of polydisperse ligand by nucleophilic ring opening addition of the epoxy and/or azlactone ring.

Toyo Pearl HW70EC (TosoHaas)
Toyo Pearl HW65EC (TosoHaas)
Toyo Pearl AF650M (TosoHaas)
Eupergit C250L (Röhm)
Eupergit 250 (Röhm)
Fractogel EMD Epoxy (M) (Merck)
Fractogel EMD Azlactone (S) (Merck)
Poros EP (Perkin Elmer-Biosystems)

Fines were removed by repeated washing with saline and filtered through 20 μm and 50 μm woven nets, respectively. The beads were then soaked in acetone for 24 hrs.

2. Activated Membranes:

Microfiltration hollowfiber (wall thickness 100 μm, inner diameter 300 μm) and flat sheet membranes (wall thickness 90 μm) with amino groups having a sieving coefficient of >95% protein from plasma were treated with ethanol solution with 3% cyanuric chloride and 1% sulfuric acid for 20 min. at room temperature in filtration mode and dried afterwards with 40° C. dried air. The amount of activation was determined by chloride titration after alkaline hydrolysis resulting in a value of 0.035 mmol Cl/g dry membrane.

EXAMPLE 1

Preparation of Adsorber Material from Activated Beads 13 g (dry weight) activated beads (e.g. Toyo Pearl HW70EC TosoHaas, Stuttgart, Germany), diameter 140 μm, were soaked in 52 g acetone for 24 hrs. The solution of the above-described polydisperse arginine ligand was mixed with the beads and gently stirred at 70° C. for six hrs. The beads were rinsed with alkaline saline/ethanol solution to remove endotoxin, washed with pyrogen-free water, and filtered in a Büchner funnel and dried in vacuum at 40° C. for four hours. The amount of polydisperse arginine ligand has been measured by fluorescence spectroscopy after alkaline hydrolysis and fluorescamine staining as 9.3 mg/g dry beads. The same reaction can be carried out using any of the bead products described above.

EXAMPLE 2

Figure 2:
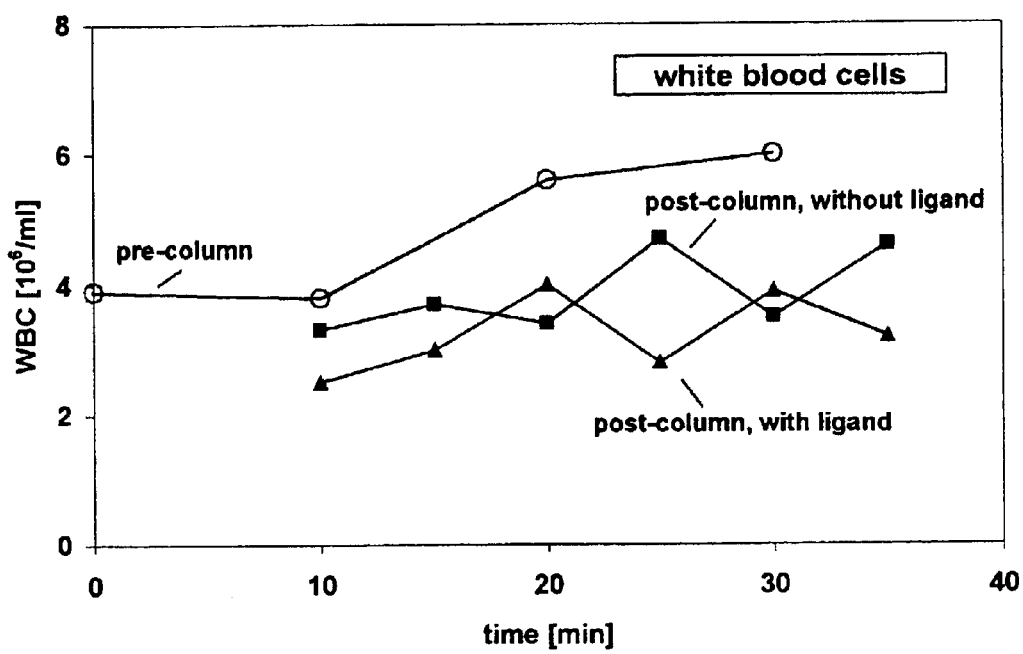
FIG. 2 shows the number of white blood cells in human blood at various time points before (0) and after (▼) passage through a column containing polydisperse arginine oligomers immobilized on beads (see Example 2 for details). Also shown are the number of white blood cells in human blood (labeled as ■) after passage through a column which did not contain polydisperse arginine oligomers.
Figure 3:
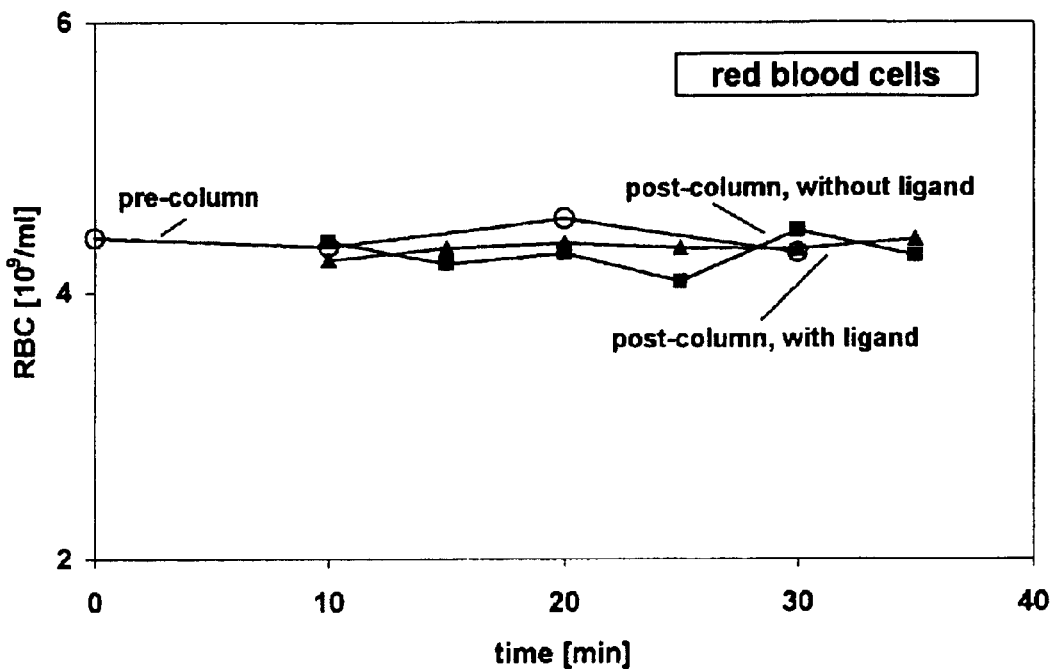
FIG. 3 shows the number of red blood cells in human blood at various time points before (0) and after (▼) passage through a column containing polydisperse arginine oligomers immobilized on beads (see Example 2 for details). Also shown are the number of red blood cells in human blood (labeled as ■) after passage through a column which did not contain polydisperse arginine oligomers.
Figure 4:
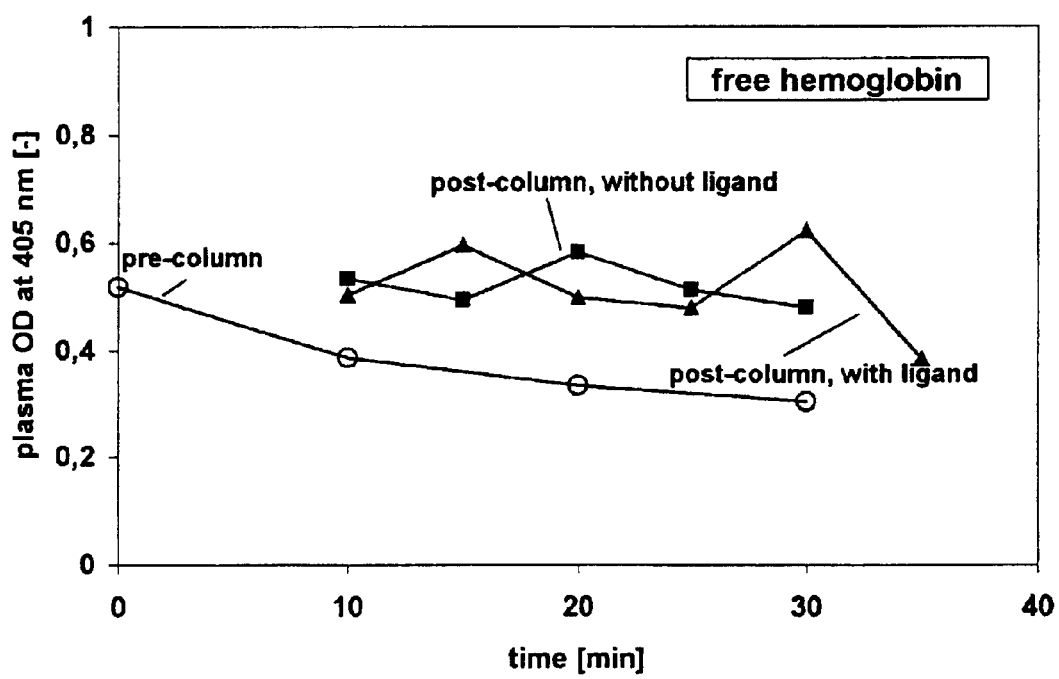
FIG. 4 shows the free hemoglobin levels in human blood at various time points before (0) and after (▼) passage through a column containing polydisperse arginine oligomers immobilized on beads (see Example 2 for details). For comparison, the free hemoglobin levels in human blood were measured (labeled as ■) after passage through a column which did not contain polydisperse arginine oligomers.
Figure 5:
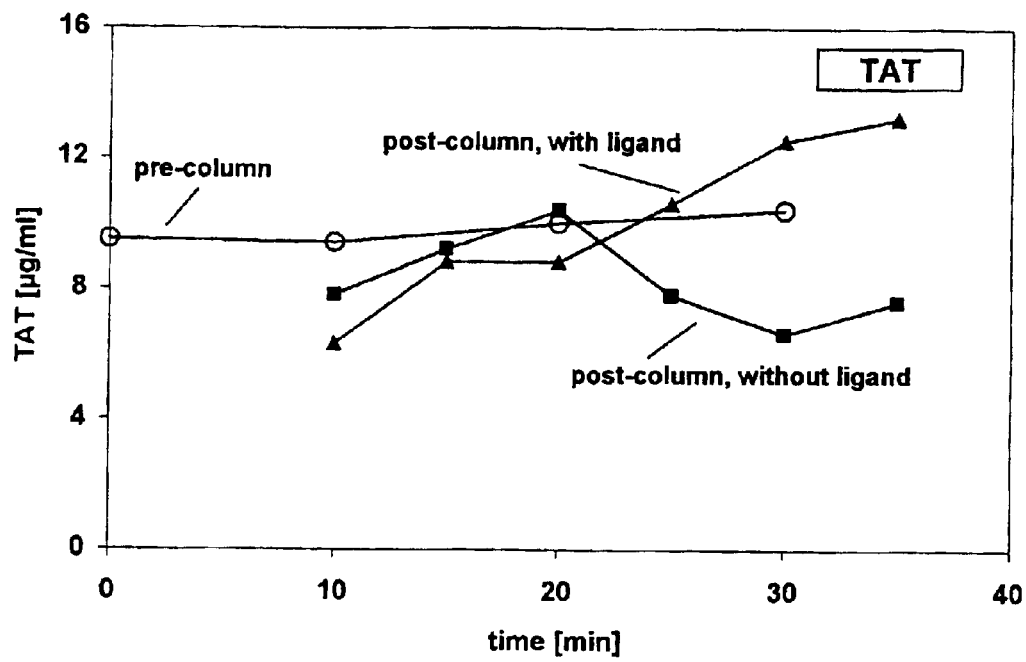
FIG. 5 illustrates the extent of thrombin-antithrombin III complex (TAT) formation of human blood at various time points before (0) and after (▼) passage through a column containing polydisperse arginine oligomers immobilized on beads (see Example 2 for details). For comparison, the human blood samples were tested similarly (labeled as ■) after passage through a column which did not contain polydisperse arginine oligomers.
Figure 6:
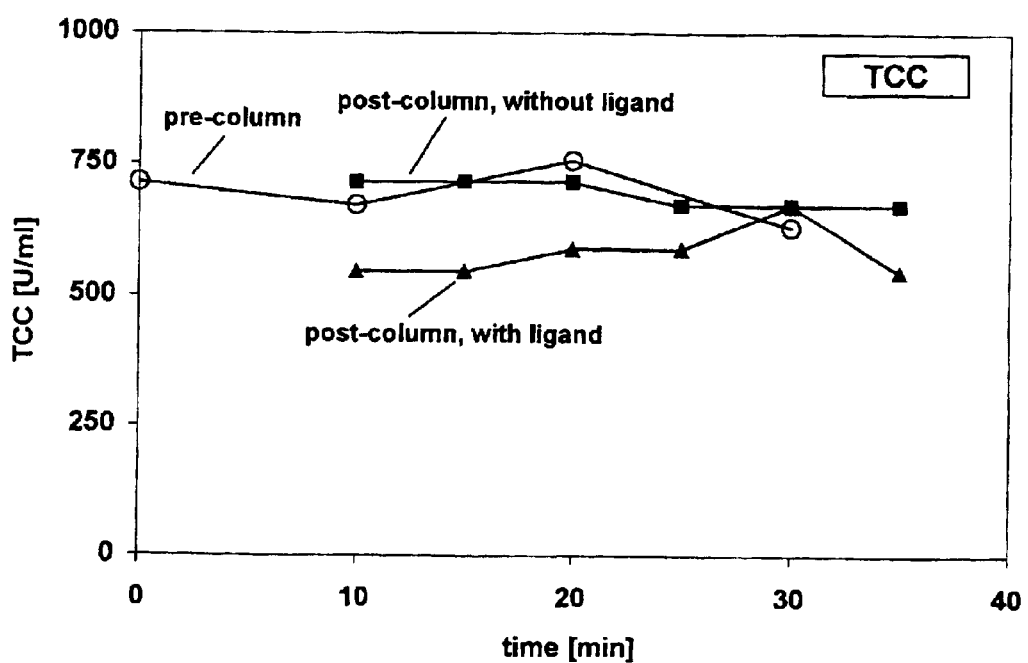
FIG. 6 illustrates the extent of terminal complement complex (TCC) activation of human blood at various time points before (0) and after (■) passage through a column containing polydisperse arginine oligomers immobilized on beads (see Example 2 for details). For comparison, the human blood samples were tested similarly (labeled as ■) after passage through a column which did not contain polydisperse arginine oligomers.

Removal of Endotoxin from Human Blood in an in vitro Single-pass System 10 g beads prepared according to example 1 were packed by gravity into small polycarbonate columns (62 mm long, 23 mm inside diameter, with a packed bed volume approximately 25 ml) and autoclaved at 121° C. for 20 min. 10 g activated beads treated similarly but not reacted with any ligand were used as control. The packing quality of the columns was characterized by common chromatographic column characterization (see G. Sofer, L. Hagel, "Handbook of Process Chrornatography", Academic Press 1997, chapter 15) to be 320 HETP (height equivalent to a theoretical plate) and 1.7 peak asymmetry (A.). Immediately prior to use, the bead-packed columns were washed with 100 ml of sterile physiological saline solution. 500 ml of fresh human blood treated with ACD was mixed with 30 EU/ml LPS isolated from *E. coli* 055:B5 (Sigma) and passed through the columns at a flow rate of 5 ml/min. Aliquots of 2 ml were taken before and after the test columns and assayed for LPS content using chromogenic Limulus Amoebocyte Lysate test (LAL) as described by K. Duner, (1993) *Journal of Biochem. and Biophys. Methods* 26:131–142. Blood cell counts, free hemoglobin, thrombin-antithrombin III complex (TAT) formation [Deppisch, R. et al. (1994) *Nephrol. Dial. Transplant* Suppl.317–23] and terminal complement complex (TCC) activation [Deppisch, R. et al. (1990) *Kidney Int.* 37:696–706] were determined for biocompatibility assessment. The results are shown in FIGS. 1 to 6.

EXAMPLE 3

Minimodules of 50 hollowfiber membranes with a length of 12–13 cm activated according to the above described method were rinsed in recirculating filtration mode for 30 min at 60° C. with a solution of 50 mg poly-L-arginine (Sigma, P7762, Mw=42,000, Mw/Mn=1.2) in 75 ml water. The membranes were washed with saline and the arginine density was determined according to the above described fluorescence method giving a value of 0.8 mg/g dried membrane.

EXAMPLE 4

According to Example 1, beads were modified with 3.3% L-arginine solution instead of the polydisperse ligand solution. The immobilized L-arginine amount was 0.43 mg/g dried beads.

EXAMPLE 5

Beads were modified according to Example 1 with 1M-ethanolamine solution as a reference ligand.

EXAMPLE 6

5 g beads were modified according to Example 1 with 100 mg poly-L-arginine (Sigma P7762, Mw=42,000, Mn/Mw=1.2) in 10 ml water. The immobilized L-arginine amount was 13.8 mg/g dried beads.

TABLE II

Comparison of dynamic capacities for endotoxin removal from human blood with different ligands immobilized on membranes.

| Ligand immobilized on membrane | Medium | Anticoagulant | Dyn. Adsorption capacity [Eu/g dried membrane] |
|---|---|---|---|
| None (pure polyethersulfone membrane) | Blood | Heparin | 60 |
| Polydisperse arginine Oligomer (example 3) | Blood | Heparin | >100 |

TABLE III

Comparison of dynamic capacities for endotoxin removal by various ligands immobilized on beads perfused with plasma or blood

| Ligand immobilized | Perfusate | Anticoagulant | LPS challenge dose [EU/ml] | Dyn. Adsorption capacity [EU/g dried beads] |
|---|---|---|---|---|
| Polydisperse arginine oligomer (example 2) | Blood | ACD | 30 | >100 |
| Polydisperse arginine oligomer (example 2) | Blood | Heparin | 10 | >50 |
| Polydisperse arginine oligomer (example 2) | Plasma | Heparin | 10 | >50 |
| Ethanolamine (example 5) | Plasma | Heparin | 10 | 10–20 |
| Polyarginine Mw = 42,000, U = 1.2 (example 6) | Plasma | Heparin | 10 | >20 |
| Arginine (example 4) | Plasma | Heparin | 10 | ~20 |
| No active ligand | Blood | Heparin | 10 | <10 |

These data show the superior dynamic adsorption capacities of the polydisperse arginine-oligomer compared to other known ligands such as polyarginine, monomeric arginine, ethanolamine, when immobilized on beads as described herein.

All references cited in the present application are incorporated in their entirety herein by reference to the extent not inconsistent herewith.

What is claimed is:

1. An endotoxin removal adsorbent comprising a ligand immobilized on a solid phase support medium, the ligand consisting essentially of a mixture of oligopeptides, of which at least one oligopeptide is a branched oligopeptide, said oligopeptides being composed of one or more amino acids having a pK>7.2, said oligopeptides being polydisperse with respect to molecular weight and to number of branches per molecule.

2. The adsorbent of claim 1 wherein the solid phase support medium is porous sufficient to allow passage of blood cells therethrough.

3. The adsorbent of claim 1 wherein the solid phase support medium is in the form of beads.

4. The adsorbent of claim 1 wherein the ligand is covalently bound to the solid phase support medium.

5. The adsorbent of claim 1, 3 or 4 wherein the amino acid is selected from the group consisting of arginine, lysine and histidine.

6. The adsorbent of claim 3 or 4 wherein said oligopeptides are polydisperse with an $R_f$ value of 0.4 or greater as measured by thin layer chromatography on silica gel using a system of $CH_3Cl_3:CH_3OH:NH_3/40:40:20$ in 45% $NH_3$ solution.

7. The adsorbent of claim 3 or 4 wherein said oligopeptides are polydisperse with an $R_f$ value of 0.6 or greater as measured by thin layer chromatography on silica gel using a system of $CH_3Cl_3:CH_3OH:NH_3/40:40\ 20$ in 45% $NH_3$ solution.

8. The adsorbent of claim 2, 4, 6 or 7 wherein the amino acid is arginine.

9. A device for extracorporeal removal of endotoxin from whole blood comprising a container which contains and retains an endotoxin removal adsorbent, wherein said endotoxin removal adsorbent comprises a ligand immobilized on a solid phase support medium, the ligand consisting essentially of a mixture of oligopeptides, of which at least one oligopeptide is a branched oligopeptide, said oligopeptides being composed of one or more amino acids having a pK>7.2, said oligopeptides being polydisperse with respect to molecular weight and to number of branches per molecule, wherein said solid phase support medium is sufficiently porous to allow passage of blood cells therethrough, and wherein said container has an inlet and an outlet positioned with respect to the adsorbent such that blood entering the inlet contacts the adsorbent before exiting the container through the outlet.

10. The device of claim 9 wherein the solid phase support medium is in the form of beads.

11. The device of claim 10 wherein the ligand is covalently bound to the beads, and the amino acid is selected from the group consisting of arginine, lysine and histidine.

12. The device of claim 9 wherein said oligopeptides are polydisperse with an $R_f$ value of 0.4 or greater as measured by thin layer chromatography on silica gel using a system of $CH_3C_3:CH_3H:NH_3/40:40:20$ in 45% $NH_3$ solution.

13. The device of claim 9 wherein said oligopeptides are polydisperse with an $R_f$ value of 0.6 or greater as measured by thin layer chromatography on silica gel using a system of $CH_3Cl_3:CH_3OH:NH_3/40:40:20$ in 45% $NH_3$ solution.

14. The device of claim 11, 12 or 13 wherein the amino acid is arginine.

15. A method for removing endotoxin from blood of an animal or human subject comprising removing a portion of blood from the subject, contacting the blood with an adsorbent wherein said adsorbent comprises a ligand immobilized on a solid phase support medium, the ligand consisting essentially of a mixture of oligopeptides, of which at least one oligopeptide is a branched oligopeptide, said oligopeptides being composed of one or more amino acids having a pK>7.2, said oligopeptides being polydisperse with respect to molecular weight and to number of branches per molecule;

whereby endotoxin is removed from the blood by adsorption to said adsorbent, then returning the blood to the subject.

16. The method of claim 15 wherein the steps of removing, contacting and returning blood are carried out in a continuous flow from and to the subject.

17. The method of claim 15 or 16 wherein the amino acid is selected from the group consisting of arginine, lysine and histidine.

18. The method of claim 17 wherein the amino acid is arginine.

* * * * *

UNITED STATES PATENT AND TRADEMARK OFFICE
CERTIFICATE OF CORRECTION

PATENT NO. : 6,774,102 B1 Page 1 of 1
APPLICATION NO. : 09/677375
DATED : August 10, 2004
INVENTOR(S) : Bell et al.

It is certified that error appears in the above-identified patent and that said Letters Patent is hereby corrected as shown below:

Title page
Item (*), Notice: delete "Subject to any disclaimer, the term of this patent is extended or adjusted under 35 U.S.C. 154(b) by 242 days." and replace with --Subject to any disclaimer, the term of this patent is extended or adjusted under 35 U.S.C. 154(b) by 273 days.--

Column 3
Line 15, delete "fictions" and replace with --functions--.

Column 4
Lines 36, 45, 52 and 59, delete "after (▼)" and replace with --after (▲)--.

Column 5
Line 1, delete "after (▼)" and replace with --after (▲)--.
Line 10, delete "after (■)" and replace with --after (▲)--.

Column 6
Line 61, delete "Cl/g dry membrane" and replace with --Cl$^-$/g dry membrane--.

Column 9, Claim 8
Line 18, delete "claims 2, 4, 6 or 7" and replace with --claims 3, 4, 6 or 7--.

Column 10, Claim 12
Line 7, delete "$CH_3C_3$:$CH_3H$:$NH_3$/40:40:20 in 45% $NH_3$ solution." and replace with --$CH_3Cl_3$:$CH_3OH$:$NH_3$/40:40:20 in 45% $NH_3$ solution.--.

Signed and Sealed this

Twenty-seventh Day of November, 2007

JON W. DUDAS
*Director of the United States Patent and Trademark Office*